United States Patent [19]

Barry et al.

[11] Patent Number: 4,666,309

[45] Date of Patent: May 19, 1987

[54] HEAD FOR MEASURING REFLECTANCE

[75] Inventors: Jürgen Barry, Munich; Karl P. Jansky, Münsing, both of Fed. Rep. of Germany

[73] Assignee: Compur-Electronic GmbH, Munich, Fed. Rep. of Germany

[21] Appl. No.: 510,461

[22] Filed: Jul. 1, 1983

[30] Foreign Application Priority Data

Jul. 14, 1982 [DE] Fed. Rep. of Germany ....... 3226370

[51] Int. Cl.4 ............................................. G01N 21/47

[52] U.S. Cl. ..................................... 356/446; 250/227

[58] Field of Search ................................ 356/445–448, 356/402, 375; 250/227; 350/96.24

[56] References Cited

U.S. PATENT DOCUMENTS

| | | | |
|---|---|---|---|
| 3,327,584 | 6/1967 | Kissinger | 250/227 X |
| 3,718,399 | 2/1973 | Kalman | 356/227 X |
| 3,806,256 | 4/1974 | Ishak | 250/227 X |
| 3,885,878 | 5/1975 | Ishak | 250/227 X |
| 3,940,608 | 2/1976 | Kissinger et al. | 250/227 |
| 4,033,698 | 7/1977 | Demsky et al. | 356/446 X |
| 4,101,222 | 7/1978 | Mathisen | 356/446 X |
| 4,464,054 | 8/1984 | Karras et al. | 356/446 |

OTHER PUBLICATIONS

Cook and Hamm, "Fiber Optic Lever Displacement Transducer", Applied Optics, vol. 18, No. 19, Oct. 1979, pp. 3230–3241.

O'Donovan and Lind, "Proximal Scanning Systems: Improved Resolution Using Inclined Optical Fibers", Applied Optics, vol. 15, No. 5, May 1976, pp. 1299–1303.

*Primary Examiner*—R. A. Rosenberger
*Attorney, Agent, or Firm*—Townsend and Townsend

[57] ABSTRACT

The present invention is with respect to a reflectance measuring head that is designed for stopping the production of false readings by regular (as opposed to diffuse) reflection and shiny parts of the sample without using normal shine traps or diaphragms. False readings as produced by regular reflection, by surface grain or structure and by inhomogeneity of the surface of the sample are furthermore put an end to by having a number of transmitters placed at an equal distance from one receiver or having a number of receivers placed at an equal distance from a transmitter. A more specially useful effect is produced if a number of transmitters and a number of receivers are placed alternately in the form of a matrix.

7 Claims, 4 Drawing Figures

HEAD FOR MEASURING REFLECTANCE

BACKGROUND OF THE INVENTION

The present invention is with respect to heads for the measurement of reflectance at a reflecting material, and using a transmitter and a receiver in the form of light guides.

Reflectance measuring heads of this sort have the purpose of measuring the reflectance at light reflecting surfaces and producing a quantitative reading in respect thereof. In known ways of measuring reflectance the readings as taken are not true readings because of the effects of glossy patches on the reflecting sample and so for turning the readings into true readings the known systems have shine traps or diaphragms that however make the apparatus much higher in price and more complex and furthermore the adjustment thereof takes more time and trouble.

SHORT OUTLINE OF THE INVENTION

It is for this reason that one purpose of the present invention is that of designing a reflectance measuring head giving readings that are true and not changed by the effects of regular reflection or shine.

For effecting this and other purposes that will come to mind on reading further parts of the present account, a measuring head for measuring reflectance of a reflecting material using a transmitter and a receiver in the form of light guides is so designed that the distance $b_1$ between the receiver and the reflecting surface of the reflecting material is given by the equation $$b_1 = \frac{\frac{1}{2} D_s + \frac{1}{2} D_e - a \tan\delta}{\tan\delta - 2 \tan\delta}$$

and the distance (x) between the axes of the received light and transmitted light guides is in keeping with the equation $$x = b_1 \cdot \tan \alpha$$

wherein $\alpha$ is the angle between the reflected light rays coming to the receiver and a line normal to the reflecting material, $\delta$ is an angle that is greater than or equal to the greatest exit or aperture angle u of the selected transmitted light guide, a is the difference between the distance of the transmitting plane from the reflecting surface on the one hand and of the receiving plane from the reflecting plane on the other, $D_s$ is equal to the diameter of the transmitted light guide and $D_e$ is equal to the diameter of the received light guide.

By keeping to the equalities given in this form of the invention it is possible for reflectance measuring heads to be produced that make certain that regularly (as opposed to diffusely) reflected light from the reflecting material does not make its way to the receiver so that shiny patches, that may be present on the reflecting surface to be measured and at which there is regular reflection, do not make for false readings or have any other undesired effects in this respect. Putting an end to such effects on the readings as caused by shining patches is possible in the present invention without the use of special gloss traps or diaphragms so that the reflectance measuring head is in fact of simple design and no adjustment measures or work are needed.

Preferably the aperture angle $\epsilon$ of the received light guide is roughly equal to $\alpha+\delta$, that is to say, $\epsilon \simeq \alpha+\delta$. This makes certain that the received light guide is able to get light from all points of the reflecting surface as illuminated by the transmitted light guide, this taking into account the full part of the area or surface illuminated by the light cone of the transmitted light guide, of the reflecting material on measuring reflectance.

The best readings when measuring reflectance are produced if the angle $\alpha$ is between 40° and 50° and more specially has the value of 45°. If the angle $\alpha$ has the value of 45° and if the direction of illumination of the reflecting surface is normal to the sample surface the best measurement of reflectance will be possible, such a system being the so-called 0°–45° system.

It is best for the receiving surface and the transmitting surface to be in a plane that is parallel to the reflectance or reflecting face. In this case, that is to say when $b_1$ is made equal to $b_2$, it is useful to have a transparent plate between the transmitting and the receiving plane on the one hand and the reflecting surface on the other, such a plate being for example a piece of glass sheet. When this is done one then has a controlled or regular distance between the transmitting and the receiving plane on the one hand and the reflecting material on the other so that there are no changes in the level of the signal or reading that might otherwise be caused by the distance not being regular. The reflecting material is placed on side of the transparent plate, opposite to the plane stretching through the transmitter and receiver plane, when measuring is done.

If the refractive index (n) of the transparent plate is about equal to 1.5 the angle $\alpha$ in the medium is to be about 28°. When this is so, the light reflected under 45° will be received, because there is a small air space (with a refractive index (1) between the reflecting material and the glass.

Preferably the aperture angle u of the transmitted light guide in a medium with a refractive index (n) of about 1.5, that is to say of a glass plate for example, is less than 14°. When this is the case regular reflection (as opposed to diffuse reflection) will be stopped with commercial quality light guides. The aperture angle $\epsilon$ of the received light guide is preferably greater than 34° if the index of refraction of the transparent plate is about 1.5. If the angle $\alpha$ has a value of about 28° and the angle $\delta$ is under 14° the sum of these angles will be roughly equal to the aperture angle, or $\epsilon \simeq \alpha+\delta$.

In keeping with a useful further development of the invention at least two receivers are placed at the same distance x from the transmitter in one plane, the distance being equal to $b_1$ times tan $\alpha$. By using a number of receivers in the form of light guides at the said distance x one has a simple way of generally putting on end to false readings as caused by the effects of structure in addition to stopping false readings being produced by surface grain or structure as well as by regular reflection. Surface structure effects are more specially common with textiles. Because of the use of more than one transmitter the reflectance radiation is averaged out so that there are no false readings for the reflectance itself caused by irregularities of a discolored surface that is, for example to be tested, such false readings otherwise causing different evaluations of the material in question.

As part of a further highly useful further development of the present invention the effects on the readings of irregularities in the structure of the surface to be tested are even further cut down by having a number of transmitters and a number of receivers placed in a single plane like a matrix alternately with an even spacing of x. Because of the symmetrical and alternating pattern or array of the transmitters and the receivers readings are produced that are almost completely free of the effects of grain, structure or irregularities in the surface of the sample that is to be tested. If the aperture angle $\epsilon$ is about equal to the sum of the angles $\alpha$ and $\delta$, that is to say $\epsilon=\alpha+\delta$, then a number of areas of the separate received light guides and which are illuminated by different cones of transmitted light, will be taken into account or covered by the reception of the light so that there will be an averaging effect and false readings that might otherwise be caused by surface irregularities and surface grain are completely put an end to.

Further useful effects and details of the invention will be seen from the account now to be given of working examples using the FIGS. 1 to 4 herein.

LIST OF DIFFERENT VIEWS OF THE FIGURES

DETAILED ACCOUNT OF WORKING EXAMPLES OF THE INVENTION

Figure 1:
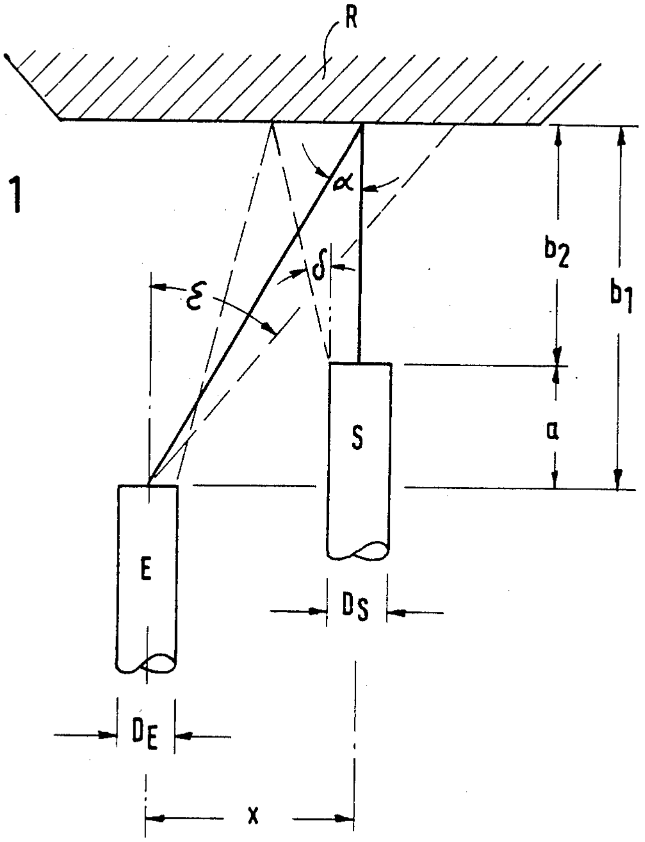
FIG. 1 is a diagrammatic view of one possible reflectance measuring head system to make clear the nature of the present invention.

In the system of FIG. 1 using a transmitter and a receiver for a reflectance measuring head the angles, distances and diameters have been marked that are important for the present invention and which have certain given values in the definition of the invention.

Figure 2:
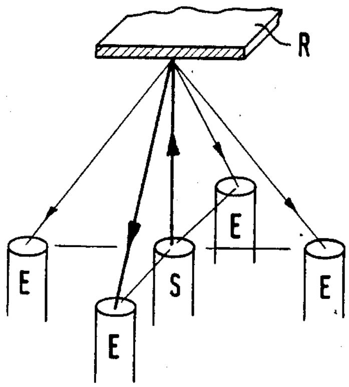
FIG. 2 is a view of a system with one transmitter and four receivers placed round it.

FIG. 2 is a view of a grid system, in which four receivers are placed symmetrically about a transmitter. The light reflected from the reflecting material R goes to four different receivers so that there are four different reflectance directions, in which the reflectance is measured. The averaging effect produced with this system takes care of the effects of surface grain or structure of the reflecting material that might otherwise be responsible for false reflectance readings.

Figure 3:
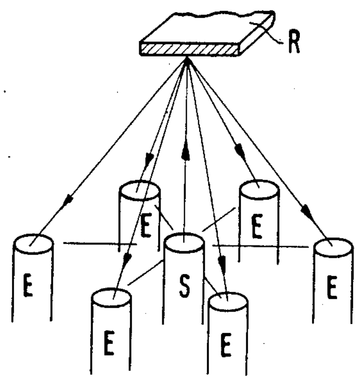
FIG. 3 is a view of a transmitter with six receivers placed about it.

In FIG. 3 a form of the invention will be seen in the case of which the transmitter has six receivers placed about it so that the reflectance is measured in six different directions with the outcome that there is an even better averaging effect putting an end to the effects of surface grain or markings to an even greater degree when readings are taken for reflectance. In the FIGS. 2 and 3 the positions of the receivers and transmitters may be changed over. In such a case the invention may be worked with quite the same effect.

Figure 4:
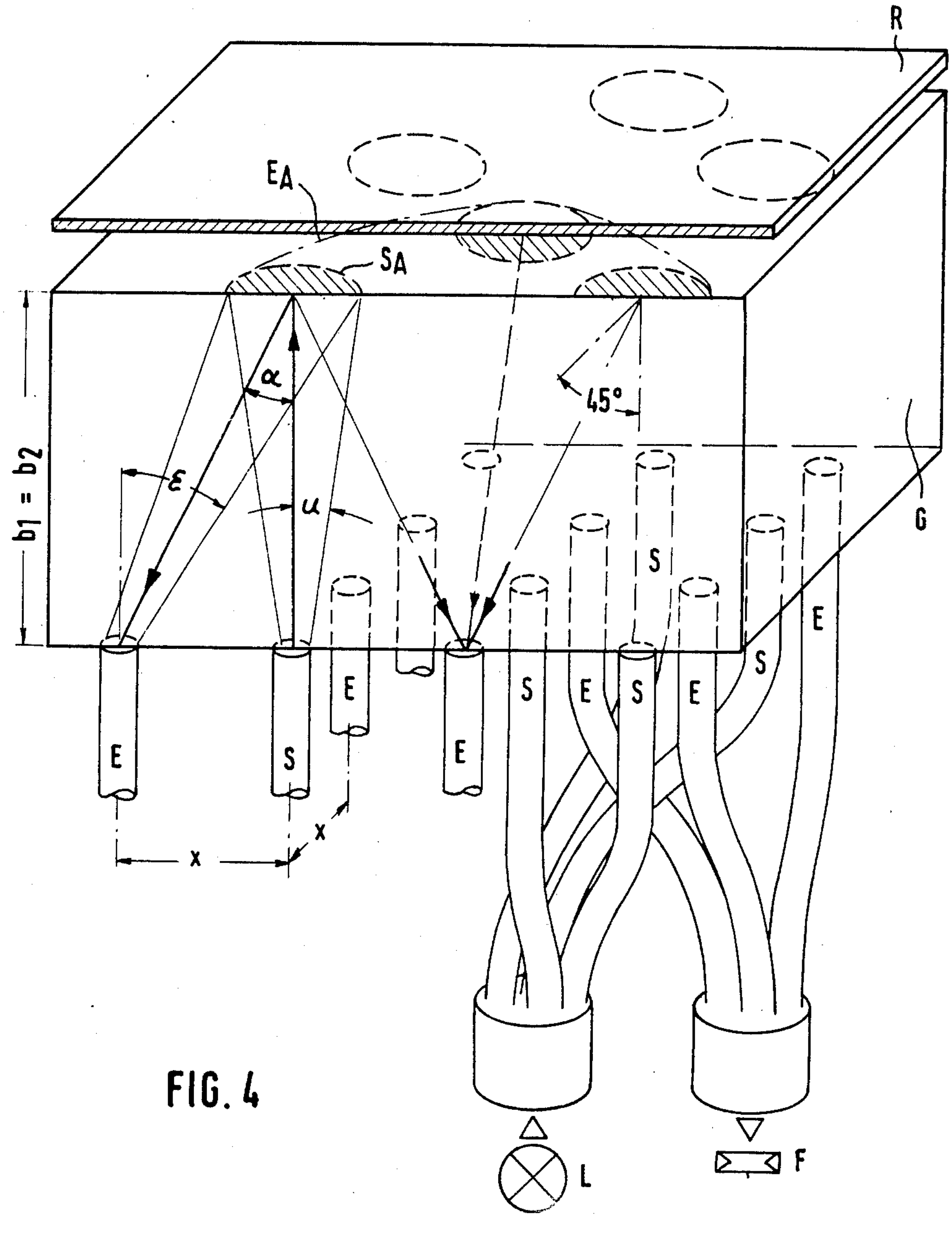
FIG. 4 is a view of a matrix-like system using a number of transmitters and a number of receivers.

In the case of the reflectance measuring head to be seen in FIG. 4 the light coming from a light source L is guided by a group of transmitters S in the form of light fiber guides to the outlet or exit faces of the fiber guides, such outlet faces being in a single plane. In the same way light coming to the inlet or entry faces of the receivers, that are in the form of light fiber guides, is guided to a photo-receiver F producing a representative signal that goes to a measuring system. The inlet faces of the receivers are in this case in the plane as defined by the outlet planes of the transmitters.

Between the reflecting material R and the plane as defined by the transmitters and receivers there is a transparent plate G with a thickness of $b_1=b_2$. On the left hand side of the FIG. 4 the light paths as marked in FIG. 1 have been made clear once again. A beam from the transmitter S makes its way parallel to the line that is parallel to the reflecting surface of the reflecting material R to the said surface. This beam is marked with a thick line. After reflectance at the reflecting surface the beam goes to one receiver E at an angle $\alpha$.

On the left hand side of FIG. 4 the transmitter aperture fields SA or the transmitter aperture angles u and the receiver aperture filed EA or the receiver angle aperture $\epsilon$ have been marked.

It will at once be seen from FIG. 1 that the inlet planes of the receiver light fibers guides get reflected radiation that is emitted from a number of transmitters or from different transmitters, insofar as there are a number of transmitter aperture fields SA of different transmitters in the receiver aperture field EA. This being so, the reflected or reflectance radiation is averaged out on being received so as to take care of further effects as caused by grain structure or inhomogeneity of the reflectance surface.

Between the glass plate G with an index (n) of refraction of about 1.5 and the reflecting surface R there is an air gap so that inlet face of the receiver light fiber guide is able to "see" or take up the radiation reflected under 45°.

The account of the invention has been given on the footing of preferred working examples thereof. Those in the art will know of a large number of different forms and changes in the apparatus of the invention without giving up the main teachings and ideas thereof. To give an example of one such possible change, the place of the transmitter in FIG. 1 might be taken by a receiver, or the other way round (so that there would be a so-called 45°–0° system unlike the 0°–45° system figured), in the case of which the same relationships are still true and the same useful effects of the invention are produced.

We claim:

1. A measuring head for measuring diffusely reflected light from the reflecting surface of a reflecting material while minimizing the measurement of regularly reflected light from the reflecting surface, the measuring head comprising:

- a transmitter including a transmitter axis;
- a receiver defining a receiver axis and a receiver aperture angle $\epsilon$, the receiver aperture angle $\epsilon$ defining a light acceptance cone;
- a first light guide having a first diameter;
- a plurality of second light guides each having a second diameter;
- the transmitter including a chosen one of the first and second light guides while the receiver includes the other of the first and second light guides;
- the transmitter being adapted to create a conically diverging transmitted light beam to create an illuminated area on the reflecting surface, the transmitted light beam having a transmitter aperture angle u, the receiving being adapted to accept light reflected from the reflecting surface along the light acceptance cone;

the transmitter and receiver alternately positioned at an equal spacing from each other in the form of a matrix;

the receiver positioned substantially outside of a cone of regularly reflected light from the reflecting surface to minimize receipt of regularly reflected light;

the receiver aperture angle being substantially equal to the sum of a first angle $\alpha$ and a second angle $\delta$, the second angle $\delta$ being equal to or greater than the transmitter aperture angle u, wherein the first angle $\alpha$ is an angle between reflected light rays coming to the receiver and a line normal to the reflecting surface and wherein the second angle $\delta$ is an angle substantially equal to or greater than the transmitter aperture angle u; and the receiver aperture angle $\epsilon$ being sized and the receiver being positioned relative to the reflecting surface so that the light acceptance cone of the receiver encompasses substantially the entire illuminated surface to maximize receipt of diffusely reflected light.

2. The measuring head as claimed in claim 1 wherein the said angle $\alpha$ has a value between 40° and 50°.

3. The measuring head as claimed in claim 1 wherein the said angle $\alpha$ is in substance equal to 45°.

4. The measuring head as claimed in claim 1 wherein the distances between the transmitter and the reflecting surface and between the receiver and the reflecting surface are equal to each other, said head further comprising a transparent plate, including transmitting and receiving planes, with an index (n) of refraction generally equal to 1.5 between the transmitting plane and the receiving plane on one hand and the reflecting surface of the reflecting material on the other.

5. The measuring head as claimed in claim 4 wherein said angle $\alpha$ has a value of 28°.

6. The measuring head as claimed in claim 1 comprising at least two receivers each placed at a distance x from the transmitter in one plane.

7. The measuring head as claimed in claim 1 wherein the transmitter and receiver are oriented parallel to one another and perpendicular to the reflecting surface.

* * * * *